(12) United States Patent
Weisenberger et al.

(10) Patent No.: US 8,295,910 B1
(45) Date of Patent: Oct. 23, 2012

(54) IMAGING METHOD FOR MONITORING DELIVERY OF HIGH DOSE RATE BRACHYTHERAPY

(75) Inventors: Andrew G. Weisenberger, Yorktown, VA (US); Stanislaw Majewski, Yorktown, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 1028 days.

(21) Appl. No.: 11/985,680

(22) Filed: Nov. 16, 2007

(51) Int. Cl.
*A61B 5/05* (2006.01)
(52) U.S. Cl. ........ 600/424; 600/439; 600/407; 600/436; 601/2; 601/3
(58) Field of Classification Search .......... 600/407, 600/437–461, 424, 436; 601/2, 3
See application file for complete search history.

(56) References Cited

U.S. PATENT DOCUMENTS

| | | | |
|---|---|---|---|
| 5,931,774 A * | 8/1999 | Williams et al. ................ 600/2 |
| 2004/0054248 A1* | 3/2004 | Kimchy et al. .................. 600/3 |
| 2006/0183960 A1* | 8/2006 | Sioshansi et al. ............... 600/3 |
| 2007/0055144 A1* | 3/2007 | Neustadter et al. ........... 600/425 |
| 2009/0127459 A1* | 5/2009 | Neustadter et al. ........ 250/336.1 |
| 2010/0025587 A1* | 2/2010 | Benlloch Baviera et al. 250/362 |

* cited by examiner

*Primary Examiner* — Brian Casler
*Assistant Examiner* — Joel Lamprecht

(57) ABSTRACT

A method for in-situ monitoring both the balloon/cavity and the radioactive source in brachytherapy treatment utilizing using at least one pair of miniature gamma cameras to acquire separate images of: 1) the radioactive source as it is moved in the tumor volume during brachytherapy; and 2) a relatively low intensity radiation source produced by either an injected radiopharmaceutical rendering cancerous tissue visible or from a radioactive solution filling a balloon surgically implanted into the cavity formed by the surgical resection of a tumor.

5 Claims, 2 Drawing Sheets

IMAGING METHOD FOR MONITORING DELIVERY OF HIGH DOSE RATE BRACHYTHERAPY

The United States of America may have certain rights to this invention under Management and Operating Contract DE-ACO5-060R23177 from the United States Department of Energy.

FIELD OF THE INVENTION

The present invention relates to brachytherapy and more particularly to a method for simultaneously imaging the radiation sources being applied and it relative location to tissue undergoing treatment.

BACKGROUND OF THE INVENTION

High dose rate brachytherapy has replaced low dose rate treatment of gynecological cancer and is being increasingly used for the treatment of breast, lung and prostate cancers. The challenge in the use of this therapy is to verify that the highly radioactive 10 Ci pellet of Ir-192 is delivered accurately and reproducibly to one or multiple source dwell positions that are selected in the target tumor volume. For multiple fractions delivered over 1 to 5 days/weeks, the reproducibility of source placement and the resultant dosimetry cannot, at this time, be directly verified. Usually, in such treatment, a dummy source is tracked in the target volume to check the mechanical aspects of the source insertion and delivery to the appropriate locations(s) (the source is attached to the end of a stainless steel wire for insertion and removal) through a single or an array of catheters and afterwards, in subsequent treatments, the source is assumed to be delivered to the designated locations(s).

As depicted schematically in attached FIGS. 1 and 2, balloon brachytherapy is implemented in a MammoSite brachytherapy applicator that is intended to deliver intracavity radiation to the surgical margins after, for example, a lumpectomy. In accordance with this well known procedure, a balloon 10 is inserted via a catheter 12 in the breast 14 in the post-surgical cavity formed during, for example, a lumpectomy. A radioactive source 16 is then inserted into the center of balloon 10 to kill any remaining residual cancer cells to prevent local cancer recurrence. Catheter 12 is a double lumen balloon catheter that is surgically inserted into the tumor bed during a lumpectomy procedure or post lumpectomy during a separate open or ultrasonically guided closed procedure within ~10 weeks of surgery. A more complete description of the MammoSite procedure can be found at the following website, http://www.mammosite.com/breast-lumpectomy/how-it-works.cfm.

U.S. Pat. No. 6,847,838 to Macey et al. describes a technique employing 2 miniature gamma cameras to acquire stereo images of an Ir-192 pellet as it is moved in a target tumor volume. This pinhole imaging technique provides 3-D images of the source as it moves and stops at designated locations in the body non-invasively and with no impact on the treatment procedure. The dwell times and locations of the Ir-192 pellet are tracked by recording each spot image captured as separate frames in a composite summed image. Temporal acquisition and retrospective analysis of this series of dynamic images allows for the removal of the interference of adjacent dwell points in the same catheter and adjacent catheters. The typical range of dwell times employed to produce the desired dose distribution in the target volume extends from 0.5 to 20 seconds and source positions separated by 2.5 to 50 mm. The resulting dose distribution calculated from the individual captured image data set is compared with the planned dose prescribed for the target volume. This method should be able to detect local and global differences in these dose distributions that result from the limited accuracy and reproducibility of placing the Ir-192 pellet source in multiple catheters that can bend and change position within the limits of immobilization that can be set for soft tissue masses in the body. This method does not, however, provide for direct monitoring in-situ of the cancer target.

Thus, there currently exists no accurate, reliable and reproducible method for determining the location of the source in a target area in-situ during brachytherapy treatment.

OBJECT OF THE INVENTION

It is therefore an object of the present invention to provide an accurate, reliable and reproducible method for determining the location of the radioactive source in a designated target area during brachytherapy.

SUMMARY OF THE INVENTION

According to the present invention there is provided a method for in-situ monitoring both the balloon/cavity and the radioactive source in brachytherapy treatment utilizing at least one pair of miniature gamma cameras to acquire separate images of: 1) the radioactive source as it is moved in the tumor volume during brachytherapy; and 2) a relatively low intensity radiation source produced by either an injected radiopharmaceutical rendering cancerous tissue visible or from a radioactive solution filling a balloon surgically implanted into the cavity formed by the surgical resection of a tumor.

DETAILED DESCRIPTION

The novel method of the present invention makes either the breast tissue or the outline of the balloon visible to one or a set of gamma cameras implemented to image Tc-99m or similar low intensity radioactive pharmaceutical in order to see the location of the cavity/balloon while at the same time imaging the high intensity Ir-192 pellet source using a different or set of different gamma cameras built to image a high intensity radioactive source. By registering the relative positions of the post-surgical cavity/balloon and the Ir-192 pellet, the correct dose to the cavity tissue can be determined.

Figure 2:
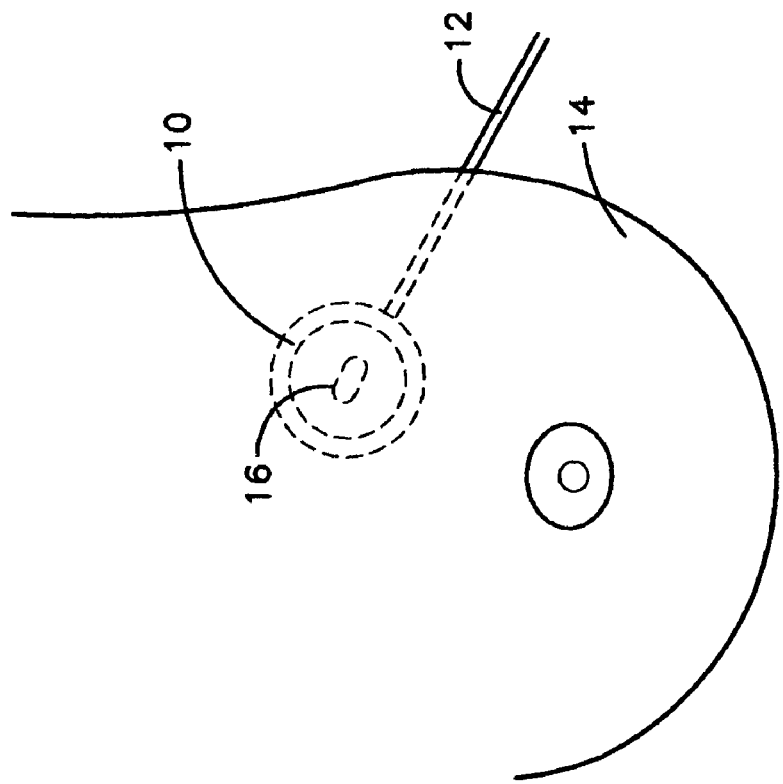
FIG. 2 is a schematic representation of the insertion of a radioactive seed into the center of the balloon as practiced in the MammoSite practice.
Figure 1:
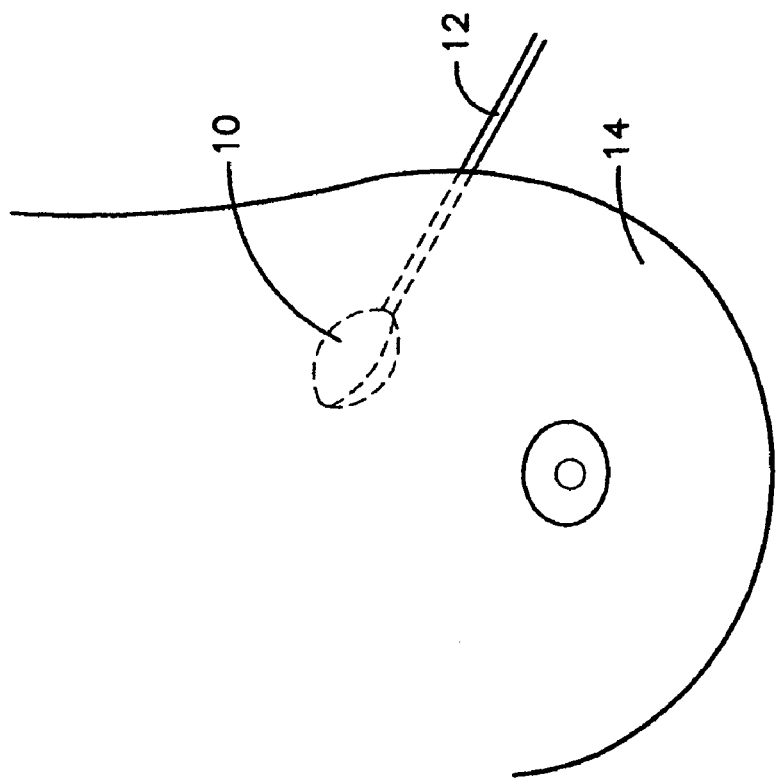
FIG. 1 is a schematic representation of the insertion of a MammoSite balloon into the breast as practiced in the prior art.

Referring now to the accompanying drawings that depict alternative embodiments of the method of the present invention, according to the embodiment depicted in FIG. 2, a first miniature gamma camera 18 including a parallel collimator 20 designed to image a low intensity pharmaceutical which is present in balloon 10 or breast tissue 14 after injection thereof in accordance with conventional practice is place din proximity with breast 14. A second miniature gamma camera 22 equipped with a pinhole collimator 24 designed to image the radioactivity produced by high intensity radioactive pellet 16 is similarly located in proximity with breast 14. The simultaneous acquisition of images from gamma cameras 18 and 22 and resolution of the two thus acquired images provides the following in-situ information: 1) the position of the surface of the balloon and breast cavity; 2) the position of the Ir-192 source relative to the treated tissue; 3) confirmation of the source position(s) and time(s) during the treatment procedure; and 4) input data fro does calculation in breast tissue.

Figure 4:
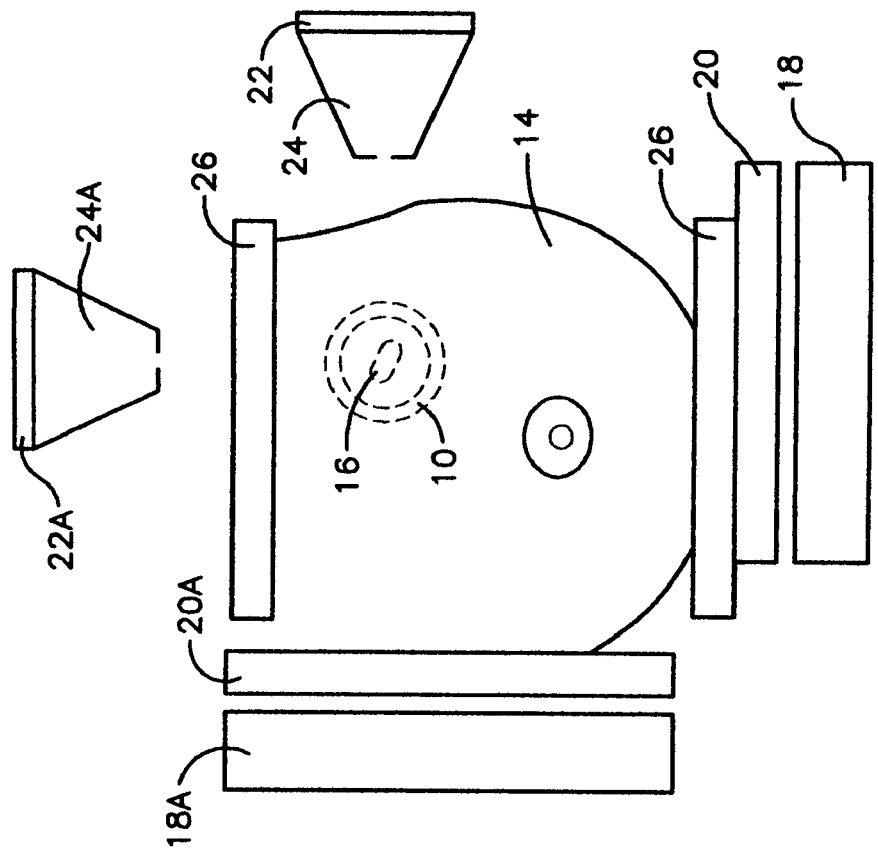
FIG. 4 is a schematic diagram showing the positioning of two sets of gamma cameras to obtain stereotactic images of the MammoSite practice in accordance with an alternative embodiment of the present invention.
Figure 3:
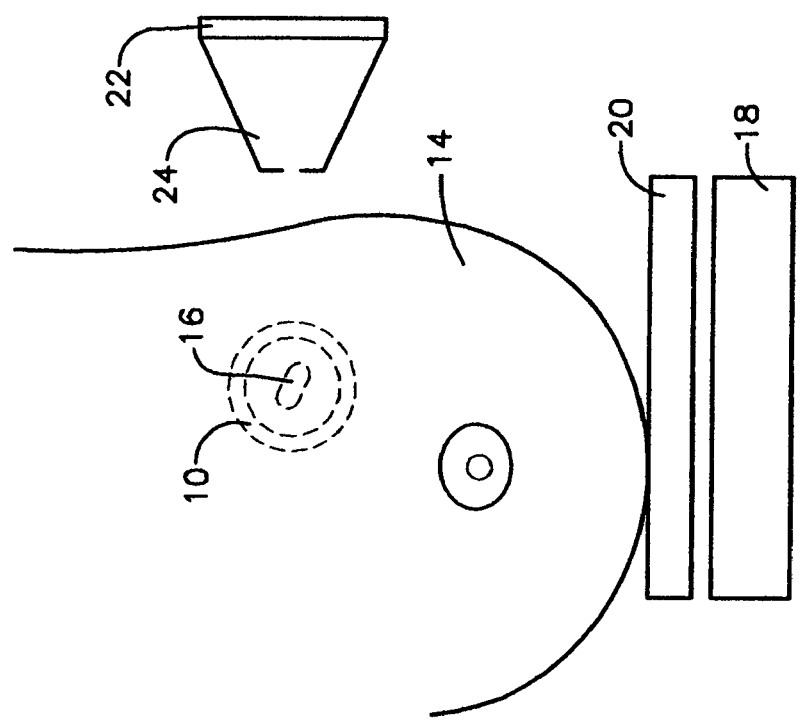
FIG. 3 is a schematic diagram showing the positioning of gamma cameras in accordance with the practice of the present invention.

In the embodiment of the present invention depicted in FIG. 4, pairs of pinhole collimator equipped gamma cameras 22 and 22A and parallel collimators 18 and 18A are utilized to provide stereotactic views of the balloon/cavity and radioactive seed locations. Also shown in FIG. 4 are a pair of radiation permeable compression paddles 26 that may be used to further immobilize the breast under treatment and thus further enhance the accuracy and reproducibility of the resulting images.

Parallel hole and pinhole equipped gamma cameras are well known in the art and their descriptions included in the aforementioned U.S. Pat. No. 6,847,838 whose disclosure is incorporated herein in its entirety for a description of such well known prior art devices.

As will be apparent to the skilled artisan, the low intensity pharmaceutical required for the acquisition of the image by parallel hole collimator equipped gamma camera(s) 18 and 18A may be injected into either balloon 10 or into the body of the patient undergoing treatment so long as it is present in the amounts necessary to top provide distinction between the image of the area of cavity/balloon 10 and the location of radioactive seed 16.

There has thus been described a method of imaging brachytherapy treatment in-situ that provides non-invasively the following critical information: 1) the position of the surface of the balloon and breast cavity; 2) the position of the Ir-192 source relative to the treated tissue; 3) confirmation of the source position(s) and time(s) during the treatment procedure; and 4) input data fro does calculation in breast tissue.

As the invention has been described, it will be apparent to those skilled in the art that the same may be varied in many ways without departing from the spirit and scope of the invention. Any and all such modifications are intended to be included within the scope of the appended claims.

What is claimed is:

1. A method for directly monitoring in-situ both the balloon/cavity and the radioactive source in brachytherapy treatment comprising:
    A) introducing a high intensity non-liquid radioactive source and a relatively low intensity liquid radiation source into a patient:
    B) simultaneously acquiring separate images of: 1) said high intensity non-liquid radioactive source emitting photon radiation at one particular photon energy as it is moved in a tumor volume during brachytherapy; and 2) said relatively low intensity liquid radiation source produced by either an injected radiopharmaceutical rendering cancerous tissue visible or by a radioactive solution filling a balloon surgically implanted into the cavity formed by the surgical resection of a tumor; said low intensity liquid radiation source emitting photons at a different energy than the non-liquid radioactive source;
    C) registering the two thus acquired images of two different photon energies; and
    D) displaying said images.

2. A method for directly monitoring in-situ both the balloon/cavity and the radioactive source in brachytherapy treatment comprising:
    A) introducing a high intensity non-liquid radioactive source and a relatively low intensity liquid radiation source into a patient;
    B) acquiring separate images of 1) said high intensity non-liquid radioactive source emitting photon radiation at one particular photon energy as it is moved in a tumor volume during brachytherapy; and 2) said relatively low intensity liquid radiation source produced by either an injected radiopharmaceutical rendering cancerous tissue visible or by a radioactive solution filling a balloon surgically implanted into the cavity formed by the surgical resection of a tumor; said low intensity liquid radiation source emitting photons at a different energy than the non-liquid radioactive source, wherein said separate images are acquired in such temporal proximity so as to permit accurate spatial co-registration of said images; and
    C) co-registering the two thus acquired images of two different photon energies.

3. The method of claim 2 wherein said separate images are acquired at or about the same time.

4. The method of claim 2 wherein the acquisition of said image of said high intensity non-liquid radioactive source and the acquisition of said low intensity liquid radiation source commence at the same time.

5. A method for directly monitoring in-situ both the balloon/cavity and the radioactive source in brachytherapy treatment comprising:
    A) introducing a high intensity non-liquid radioactive source into a tumor volume;
    B) introducing relatively low intensity liquid radiation source into a patient;
    C) concurrently acquiring separate images of said radioactive source and said radiation source through the steps of:
        (i) utilizing a pinhole collimated gamma camera to acquire an image of said high intensity non-liquid radioactive source emitting photon radiation at one particular photon energy as it is moved in said tumor volume during brachytherapy; said pinhole collimated gamma camera including a low density scintillator optically coupled to an area sensitive scintillator-photon detector whereby said gamma camera is able to discriminate the energy of the photons from the high intensity radioactive source form photons emitted from the low intensity radioactive source;
        (ii) utilizing a parallel hole collimated gamma camera to acquire an image of said relatively low intensity liquid radiation source produced by either an injected radiopharmaceutical rendering cancerous tissue visible or by a radioactive solution filling a balloon surgically implanted into the cavity formed by the surgical resection of a tumor; said low intensity liquid radiation source emitting photons at a different energy than the non-liquid radioactive source; and
    D) registering the two thus acquired images of two different photon energies.

* * * * *